(12) United States Patent
Soh et al.

(10) Patent No.: US 8,057,783 B2
(45) Date of Patent: Nov. 15, 2011

(54) METHOD OF INJECTING LIQUID AGENTS AT ACUPUNCTURE POINTS TO ARRIVE INTERNAL ORGANS AND METHOD OF VISUALIZING ARRIVAL OF LIQUID AGENTS

(75) Inventors: Kwang Sup Soh, Gwacheon (KR); Cheon Joo Choi, Kwangwon-do (KR); Min Soo Kim, Seoul (KR); Baeck Kyoung Sung, Anseong-si (KR); Vyacheslav Ogay, Seoul (KR)

(73) Assignees: Seoul National University Industry Foundation, Seoul (KR); Mobase Co., Ltd., Bupyeong-gu, Inchon-si (KR)

( * ) Notice: Subject to any disclaimer, the term of this patent is extended or adjusted under 35 U.S.C. 154(b) by 880 days.

(21) Appl. No.: 12/040,478

(22) Filed: Feb. 29, 2008

(65) Prior Publication Data

US 2009/0098058 A1    Apr. 16, 2009

(30) Foreign Application Priority Data

Oct. 11, 2007  (KR) .......................... 10-2007-0102600

(51) Int. Cl.
 *A61K 49/00* (2006.01)
 *A61B 19/00* (2006.01)
 *A61H 39/02* (2006.01)
(52) U.S. Cl. ........................ 424/9.1; 128/907; 600/548
(58) Field of Classification Search .................. None
 See application file for complete search history.

(56) References Cited

U.S. PATENT DOCUMENTS 3,852,413 A * 12/1974 Cammarata .................. 424/1.69

OTHER PUBLICATIONS

Byung-Cheon Lee et al. Novel Threadlike Structures (Bonghan Ducts) Inside Lymphatic Vessels of Rabbits Visualized With a Janus Green B Staining Method, The Anatomical Record (Part B: New Anat.) 286B:1-7, 2005.*
Hak-Soo Shin et al., Feulgen Reaction Study of Novel Threadlike Structures (Bonghan Ducts) on the Surfaces of Mammalian Organs, the Anatomical Record (Part B: New Anat.) 284B:35-40, 2005.*
Hyeon-Min Johng et al., Use of Magnetic Nanoparticles to Visualize Thereadlike Structures Inside Lymphatic Vessels of Rats, Advance Access Publication Aug. 30, 2006.*

* cited by examiner

*Primary Examiner* — Michael G Hartley
*Assistant Examiner* — Nabila Ebrahim
(74) *Attorney, Agent, or Firm* — Lowe Hauptman Ham & Berner LLP

(57) ABSTRACT

Provided are a method of injecting a visualizing material into a point in the vicinity of the Jung-Wan and a method of visualizing arrival of liquid agent in order to verify that the visualizing material injected arrives at internal organs. A point having the lowest electric resistance is found in the vicinity of Jung-Wan of the subject by using an electro acupuncture point detector. The visualizing material is injected into the point by means of an injecting instrument and then verified at least one point of the pancreas and the threadlike structures on top of the surface of the pancreas. The visualizing material is an alcian blue solution or a nanoparticle-containing solution labeled with fluorescent organic material.

8 Claims, 5 Drawing Sheets

METHOD OF INJECTING LIQUID AGENTS AT ACUPUNCTURE POINTS TO ARRIVE INTERNAL ORGANS AND METHOD OF VISUALIZING ARRIVAL OF LIQUID AGENTS

CROSS REFERENCES

Applicant claims foreign priority under Paris Convention and 35 U.S.C. §119 to the Korean Patent Application No. 10-2007-0102600, filed Oct. 11, 2007 with the Korean Intellectual Property Office.

BACKGROUND OF THE INVENTION

1. Field of the Invention

The present invention relates to a method of verifying that liquid agents injected into acupuncture points arrive at organs, and, more specifically, to methods of injecting liquid agents and visualizing their arrival wherein a visualizing material is injected into a specific point in the vicinity of "Jung-Wan" and the arrival of such an injected visualizing material at internal organs is observed.

2. Description of the Related Art

Oriental medicine reported that there are 670 acupuncture points distributed over the whole body. In case that such acupuncture points are stimulated with a variety of methods like acupuncturing or moxibusting therapy, the flow along meridian to internal organs can be activated, and conclusively, the function of internal organs can be controlled. Therefore, acupuncture points are used as effective points for treating diseases.

Among acupuncture points, "Jung-Wan", referred to as CV12 according to the WHO standard notation, has known as an effective point for treating gastroenteropathy including gastric ulcer and gastric ptosis, and diabetes.

Although as methods of stimulating Jung-Wan in addition to traditional acupuncturing or moxibusting therapy, there have been an electric stimulating therapy (acusector) and a therapy of inserting medicine together with acupuncturing, the mechanism, that is, the particular process by which such clinical acupuncturing therapies treat diseases has not been demonstrated. Particularly, because spots into which medicine inserted into Jung-Wan is dispersed haven't been known, a scientific study couldn't be possible.

In view of Western medicine, diabetes has a close relationship with the pancreas. Particularly, since the pancreas can adjust blood glucose by decreasing or increasing the same with insulin and glucagon which are hormones produced in the pancreas, the pancreas is relevant to diabetes. However, Oriental medicine hasn't found out the relationship between Jung-Wan which is a point for treating diabetes, and the pancreas which has been found relevant to diabetes in Western medicine.

According to the Bonghan theory, there is a Bonghan duct, that is, a passage of the liquid flow extending from acupuncture points to internal organs. Therefore, according to this theory, it can be expected that if medicine is inserted into Jung-Wan, it may arrive at the pancreas, which is an organ producing insulin and glucagon.

If a relationship between Jung-Wan and the pancreas can be demonstrated based on the Bonghan theory as disclosed in the above, it may be applied to methods of treating pancreatic cancer, diabetes and so forth. Therefore, a method of verifying that the material administered into Jung-Wan reaches the pancreas is required.

SUMMARY OF THE INVENTION

The object of the present invention is to provide methods of injecting liquid agents and visualizing their arrival, wherein the visualizing material is injected into a point having the lowest electric resistance in the vicinity of Jung-Wan and arrival of the visualizing material at the pancreas is observed.

Another object of the present invention is to provide methods of injecting liquid agents and visualizing their arrival, wherein it is observed that the visualizing material arrived at the pancreas is dispersed into the threadlike structures appearing at the surface of the pancreas and the threadlike structures are connected with or penetrate into the other organs.

In order to realize the above and other objects, the present invention provides a method of visualizing arrival of liquid agents, the method comprising a step of finding a point having the lowest electric resistance in the vicinity of Jung-Wan by using an electro acupuncture point detector; a step of injecting a visualizing material into the point having the lowest electric resistance by means of an injecting instrument; and verifying the visualizing material reached at least one point of the pancreas and the threadlike structures on top of the surface of the pancreas.

The method of the invention may further comprise a step of: after the step of verifying the visualizing material, photographing tissue having the visualizing material distributed therein by a microscope to acquire images thereof. The microscope may be a selected one of a stereoscopic microscope and a fluorescence microscope.

In the method, the step of injecting the visualizing material may include inserting a needle of the injecting instrument into the subcutaneous tissue under a stereoscopic microscope.

In the method, the visualizing material may be a selected one of an alcian blue solution and a nanoparticle-containing solution labeled with fluorescent organic material.

The alcian blue solution may be prepared by dissolving an alcian blue powder into phosphate buffered saline at a concentration of 1% (0.01 mg/ml) to form a solution of pH 7.2 to 7.4, filtering the alcian blue solution through polystyrene filter having porosities of 0.2 μm diameter, and keeping the filtered alcian blue solution in a cold state at a temperature of 4° C. Further, the alcian blue solution may be injected to a point having the lowest electric resistance in an amount of 0.1 μl a minute for 2 to 3 hours by means of an injecting instrument.

Nanoparticles in the nanoparticle-containing solution may be prepared by coating cobalt-ferrite having an average size of 8 nm to 9 nm with amorphous silica shell including luminescent organic material, attaching polyethylene glycol (PEG) to the surface coated with silica shell, and dissolving the surface-treated nanoparticles into either phosphating buffered saline or distilled water to form a solution having pH 7.2 to 7.4 and a concentration of 2.0 mg/cc. The size of the surface-treated nanoparticles may range from 45 nm to 50 nm and luminescent organic material in amorphous silica shell is Rhodamine B-isothiocyanate. Further, the nanoparticle-containing solution may be injected in an amount of 0.2 ml by means of an injecting instrument.

In addition, the method of injecting the liquid agents according to the present invention comprises a step of finding a point having the lowest electric resistance in the vicinity of Jung-Wan by using an electro acupuncture point detector; and a step of injecting the liquid agents into the lowest electric resistance point detected by means of an injecting instrument so that the liquid agents can arrive at the pancreas.

As disclosed in the above, by injecting the liquid agents into Jung-Wan and verifying that the visualizing agents is dispersed into the pancreas, the present invention can be applied to a method of delivering medicine which can treat the pancreas-related diseases including diabetes, pancreatic cancer and so on by injecting medicine instead of the visualizing agents.

Further, the present invention can be applied to a method which can additionally treat diseases of the other organs by carrying medicine dispersed in the pancreas to the different organs through the threadlike structures on the pancreas.

Further, by using the methods disclosed in the above, the effect of treating diseases of the other organs as well as the pancreas can be easily improved.

DETAILED DESCRIPTION OF THE INVENTION

The present invention will now be described more fully hereinafter with reference to the embodiments below. This invention may, however, be embodied in many different forms and should not be construed as limited to the embodiments set forth herein. Rather, the disclosed embodiments are provided so that this disclosure will be thorough and complete, and will fully convey the scope of the invention to those skilled in the art. The principles and features of this invention may be employed in varied and numerous embodiments without departing from the scope of the invention.

Figure 1:
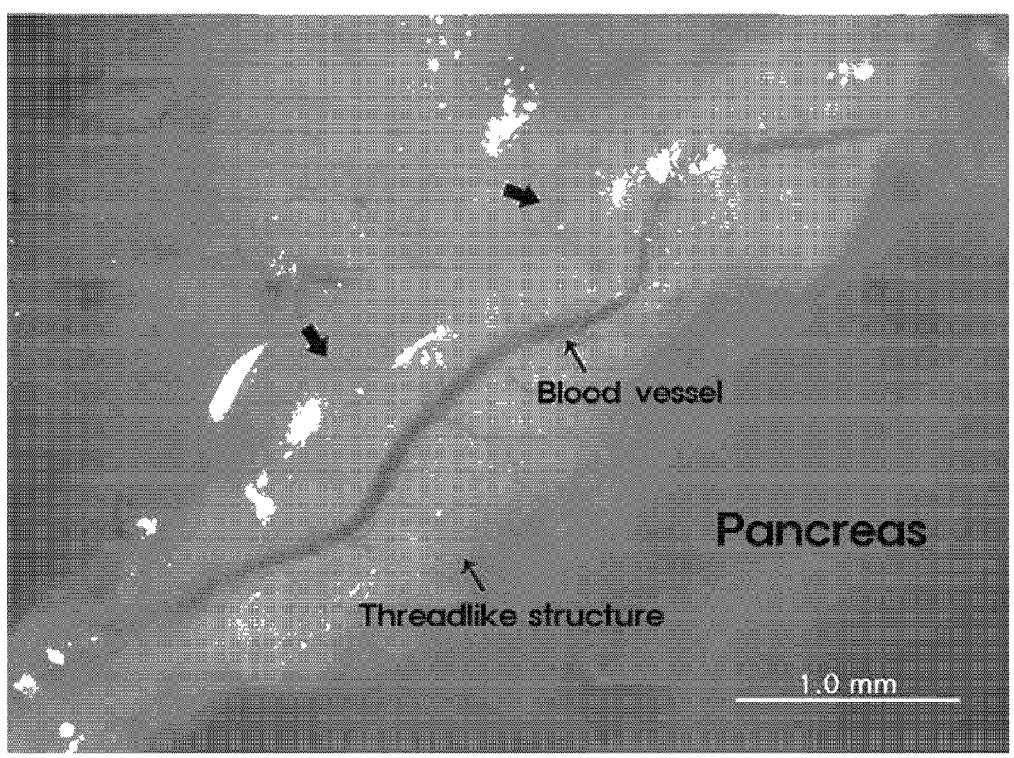
FIG. 1 is a stereoscopic image of the threadlike structures located on top of the surface of the pancreas, with being stained blue with an alcian blue solution.

FIG. 1 is a stereoscopic image of the threadlike structures located on top of the surface of the pancreas, with being stained blue with an alcian blue solution.

Referring to FIG. 1, the image shows a view that the visualizing material, that is, an alcian blue solution, administered to the animal flows into the threadlike structures of fatty streak tissue located at the surface of the pancreas, wherein the abdomen of the animal is incised and flow of the alcian blue solution into the threadlike structures on the pancreas is verified and, then, the view is photographed at a magnification of 20×. Referring to this image, the threadlike structures on the pancreas are composed of the center part where the blood vessel passes along and the transparent edge part having no fat. The thick arrows in FIG. 1 indicate the edge part of the threadlike structures having the alcian blue solution being dispersed thereinto.

The alcian blue solution is administered at the point having the lowest electric resistance in the vicinity of Jung-Wan of the animal, flows into the pancreas and, then, is dispersed into the threadlike structures located on top of the surface of the pancreas.

Since Jung-Wan cannot be specified anatomically, the point into which the visualizing material like the alcian blue solution and so on would be administered should be found by using an electro acupuncture point detector in the vicinity of the point estimated as Jung-Wan. The point into which the visualizing material would be administered is a point having the lowest electric resistance.

Figure 2:
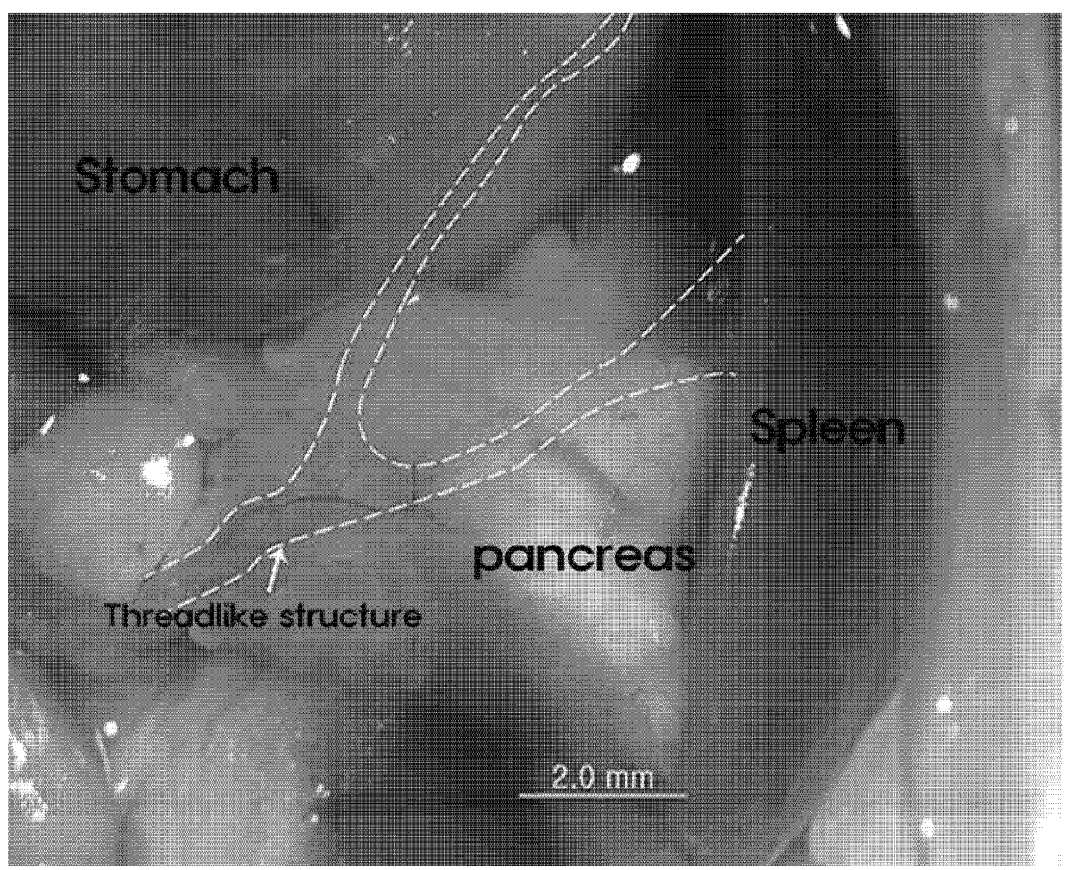
FIG. 2 is a stereoscopic image of the threadlike structures, in a different shape from ones in FIG. 1, appearing at the surface of the pancreas and connected with the spleen and the stomach.

FIG. 2 is a stereoscopic image of the threadlike structures, in a different shape from ones in FIG. 1, appearing at the surface of the pancreas and connected with the spleen and the stomach.

Referring to FIG. 2, this image shows a view of the threadlike structures having the alcian blue solution administered to the animal dispersed thereinto and connected with the spleen and the stomach wherein the threadlike structures on the pancreas are split into two ways and connected with the spleen and the stomach, respectively, and are photographed at a magnification of 7× by using the stereoscopic microscope after such view was verified. The dashed line in FIG. 2 indicates an outline along the threadlike structures connected with the spleen and the stomach. Since the threadlike structures appearing at the surface of the pancreas to extend on top of the surface of the pancreas are connected with the spleen and the stomach, the alcian blue solution flowing into the pancreas can be dispersed into the spleen and the stomach through the threadlike structures on the pancreas.

Figure 3:
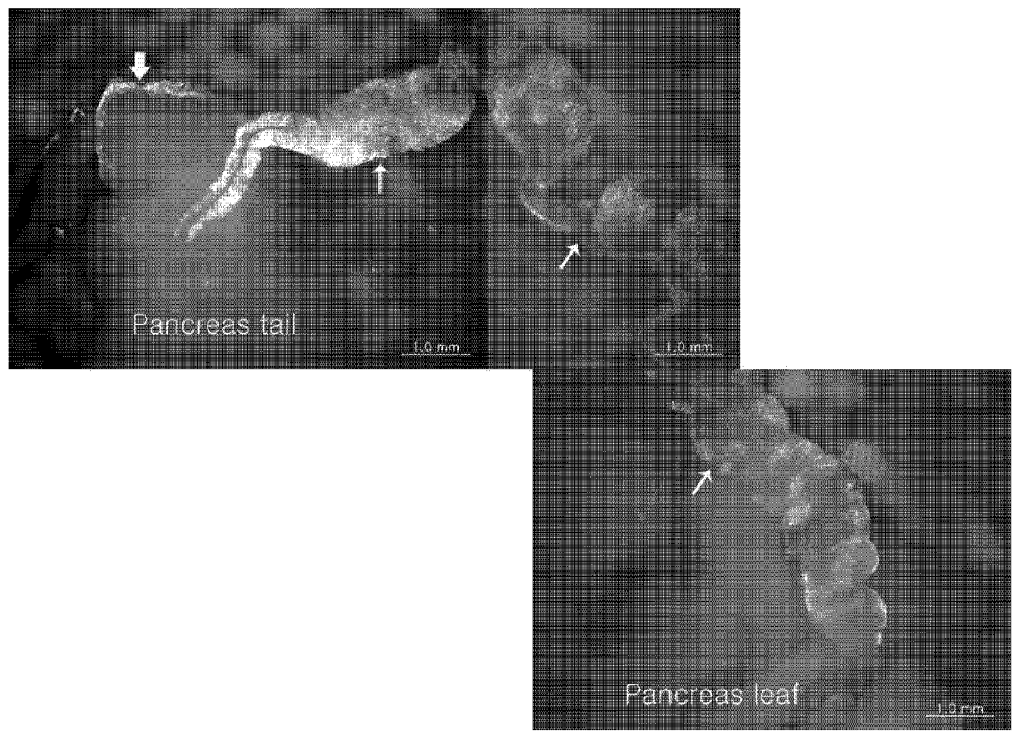
FIG. 3 is a fluorescence microscopic image of the threadlike structures, appearing at the surface of the pancreas and penetrating back into the same.

FIG. 3 is a fluorescence microscopic image of the threadlike structures appearing at the surface of the pancreas and, then, penetrating back into the same.

Referring to FIG. 3, the image shows a view that the visualizing material administered to the animal, that is, nanoparticles, flows into the pancreas and is dispersed into the threadlike structures appearing at the surface of the pancreas. The threadlike structures having nanoparticles dispersed thereinto appear at the surface of the pancreas tail and penetrate back into the pancreas leaf, and they are photographed by using a fluorescence microscope at a magnification of 10× after such view is verified. The thick arrow indicates a view of nanoparticles gathering at the pancreas tail and the other arrows indicate the threadlike structures appearing at the pancreas tail and, then, penetrating back into the pancreas leaf.

Further, nanoparticles are not distributed uniformly but scattered at the threadlike structures on the pancreas.

Figure 4A:
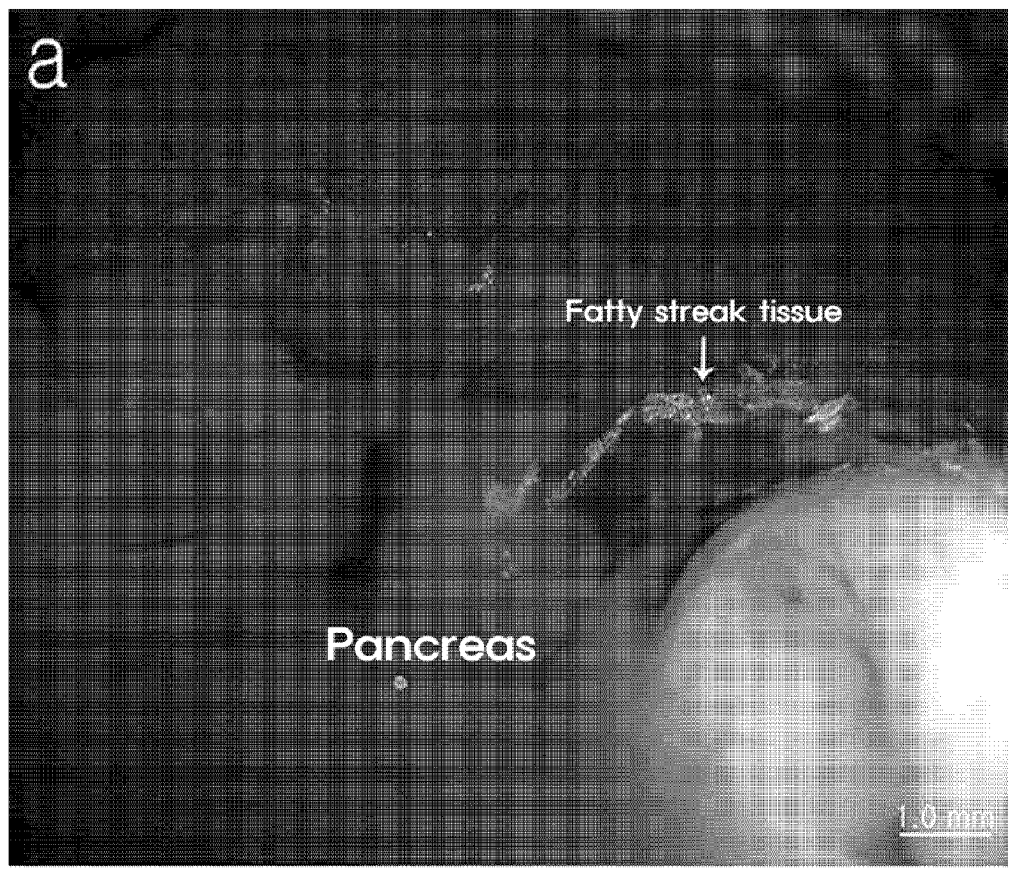
FIGS. 4A and 4B are fluorescence microscopic images of the threadlike structures appearing at the pancreas and penetrating into the spleen.
Figure 4B:
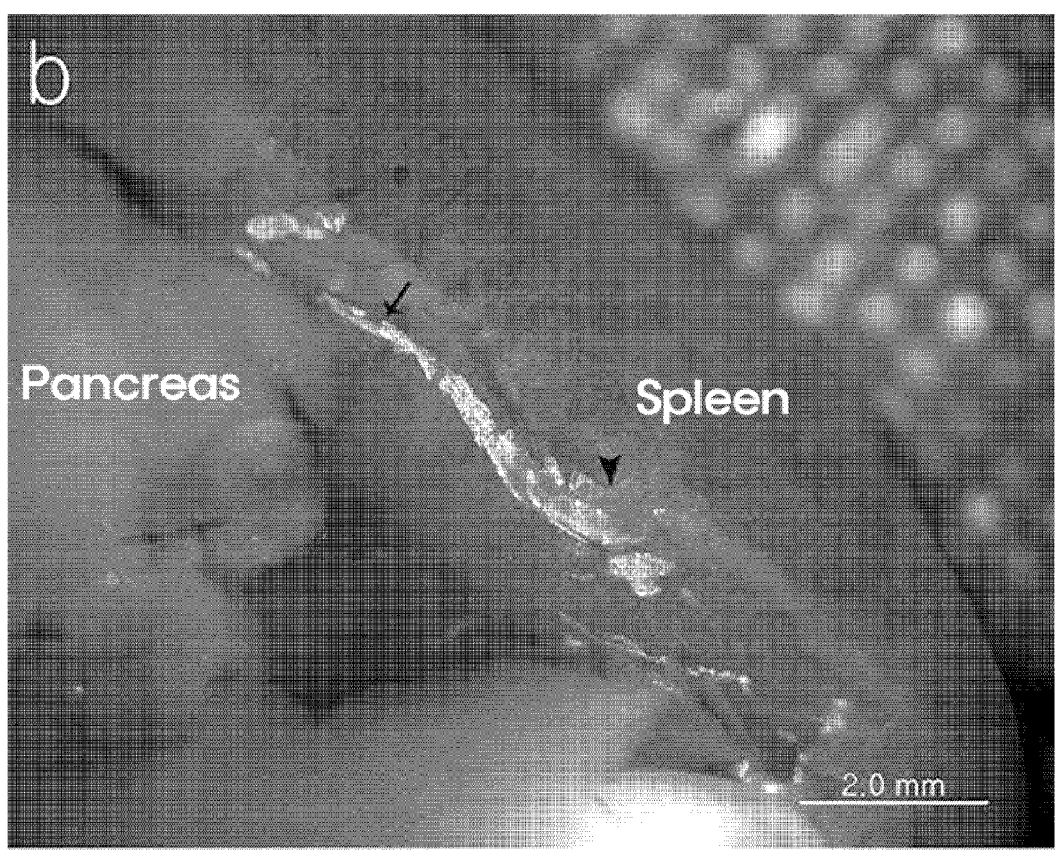

FIGS. 4A and 4B are fluorescence microscopic images of the threadlike structures appearing at the pancreas and, then, penetrating into the spleen.

Referring to FIGS. 4A and 4B, the image shows a view that after administration of nanoparticles, the pancreas, the spleen and the threadlike structures on the pancreas are detached from the animal and placed under the fluorescence microscope. FIG. 4A is a fluorescence microscopic image magnified OX wherein the threadlike structures having nanoparticles dispersed therein appear at the surface of the pancreas and extend toward the spleen. FIG. 4B is a fluorescence microscopic image magnified 7× wherein the threadlike structures extending toward the spleen penetrate into the same.

Preparation Example 1

Preparation of an Alcian Blue Solution

An alcian blue solution was prepared by dissolving an alcian blue powder into phosphate buffered solution (PBS) to a concentration of 1% (0.01 mg/ml). The alcian blue solution became a neutral solution of pH ranging from 7.2 to 7.4 by PBS. The alcian blue solution was used after being filtered through polystyrene filter having porosities of 0.2 μm size, so that particles in the alcian blue solution dissolved into PBS could not affect the flow in the organ tissue. The alcian blue solution thus prepared was kept cold at 4° C. and the period of storage should not be over a week.

Preparation Example 2

Preparation of the Fluorescent Nanoparticle-Containing Solution

Nanoparticles labeled with organic dye had cobalt-ferrite as core wherein cobalt-ferrite had the average size of 8 nm to 9 nm. Cobalt-ferrite was coated with the amorphous silica shell containing luminescent organic material, that is, rhodamine B-isothiocyanate (RITC, emission wavelength $\lambda_{max}$=555 nm). The surface of the amorphous silica shell coated might be detoxicated by having polyethylene glycol (PEG) attached thereto. The surface-treated nanoparticles of a size of 45 nm to 50 nm were used, and administration of nanoparticles larger than 50 nm into the surface of the organ might disturb flow of organ tissue.

Nanoparticles thus formed (MNP—$SiO_2$(RITC)—PEG) were dissolved into PBS or distilled water to a concentration of 1.5 to 2.0 mg/cc. The nanoparticle-containing solution had pH ranging from 7.2 to 7.4.

Example 1

For laboratory animals, the hairless mouse (males, about 6 weeks old) supplied from the JungAng Laboratory Animal Company were used. The laboratory animals were managed in a breeding cage with temperature of 23° C. and 60% relative humidity under 12 hour light/dark cycles and supplied with food and water for ad libitum access.

The care and use of the laboratory animals were in compliance with Guide for the Care and Use of Laboratory Animals, National Academy Press, 1996 and current international laws and policies.

The hairless mouse living in the above environment was anaesthetized by administering 1.5 g/kg of urethane, and all of the surgical procedures were performed under anesthesia. The hairless mouse under anesthesia were placed on the operating table under the stereoscopic microscope (Olympus SZX12) connected with the computer and the CCD camera.

Jung-Wan was determined at the middle of the umbilicus and the xiphoid process-sternum junction (JungJeong, one of acupuncture points) along the linea alba of the hairless mouse according to "GolDo method", which is a method of finding acupuncture points by using its unique measuring units. After Jung-Wan was determined, the point having the lowest electric resistance was found within a radius of 2 mm from Jung-Wan by using the electro acupuncture point detector (Hamtech Korea Co., YNS202-S) and determined as the point into which an alcian blue solution would be injected. The electro acupuncture point detector was used with a gold-plated probe of a terminal diameter of about 50 mm being additionally mounted on the electro acupuncture point detector obtained from Hamtech Korea Co. in the laboratory of the present invention.

After the point into which the alcian blue solution would be injected was found in the vicinity of Jung-Wan of the hairless mouse, a 33 gauge syringe-needle connected with micro-injector (KD Scientific, KDS310 Nanopump) and micro-manipulator was inserted into the subcutaneous tissue. It was preferable that the syringe-needle had an angle of 10 to 20 degrees from the skin surface through which the alcian blue solution would be injected. Then, the alcian blue solution prepared in the Preparation Example 1 was continuously injected in an amount of 0.1 μl a minute for 2 to 3 hours. The process of injecting the alcian blue solution was performed under the stereoscopic microscope, and it should be prevented that the syringe needle perforates through the muscular layer under the subcutaneous tissue and, thereby, the alcian blue solution flows into the abdominal cavity.

After injection was completed, the needle was removed and the hairless mouse was sacrificed by cervical dislocation method, and, then, from the umbilicus to the xiphoid process of the mouse was incised along the flank away from the injecting point by means of incision scissors. Delicate attention should be paid to prevent bleeding.

By the abdomen of the hairless mouse being cut open, the abdominal wall side surfaces of organs like the liver, the stomach, the colitis and the small intestine were observed and flow of the alcian blue solution thereinto was checked out. If the alcian blue solution flowed into the abdominal cavity, stain of the alcian blue solution on the organ surfaces could be seen. In this case, since the injection of the alcian blue solution was not properly performed, the experiment should be repeated.

If there was no stain of the alcian blue solution on the abdominal wall side surfaces of the organs, the organs were eviscerated and the portion of the pancreas was observed. Then, it was verified that the alcian blue solution was dispersed into the threadlike structures penetrating out through the surface of the pancreas and consisting of streaks of fat tissue in combination with blood vessels. Then, the images of various magnifications were observed and photographed with the stereoscopic microscope using the CCD camera and the image processing program connected thereto (FIG. 1). Further, the images wherein the threadlike structures penetrated back into the pancreas or were connected with the duodenum, the stomach and the spleen (FIG. 2) were observed through the threadlike structures having the alcian blue solution dispersed therein with the stereoscopic microscope and were photographed. FIG. 2 is the image wherein the threadlike structures on the pancreas were connected with the stomach and the spleen.

The alcian blue solution might appear at the interface tissue of the pancreas tail.

Example 2

For laboratory animals, mouse (BALB/c, males, about 8 weeks old) supplied from the JungAng Laboratory Animal Company were used. The laboratory animals were managed in a breeding cage with temperature of 23° C. and 60% relative humidity under 12 hour light/dark cycles and supplied with food and water for ad libitum access.

The care and use of the laboratory animals were in compliance with Guide for the Care and Use of Laboratory Animals, National Academy Press, 1996 and current international laws and policies.

The mouse living in the above environment was anaesthetized by administering 1.5 g/kg of urethane intraperitoneally, and all of the surgical procedures were performed under anesthesia. After hair on the abdominal side of the mouse under anesthesia was completely shaved, the mouse was placed on the operating table under the stereoscopic microscope connected with the computer and the CCD camera.

Jung-Wan was determined at the middle of the umbilicus and the xiphoid process-sternum junction (JungJeong) along the linea alba of the mouse according to "GolDo method". After Jung-Wan was determined, a point having the lowest electric resistance was found within a radius of 2 mm from Jung-Wan by using the electro acupuncture point detector (Hamtech Korea Co., YNS202-S) and determined as the point into which the nanoparticle-containing solution would be injected. The electro acupuncture point detector was used with a gold-plated probe of a terminal diameter of about 50

μm being additionally mounted on the electro acupuncture point detector obtained from Hamtech Korea Co. in the laboratory of the present invention.

After the point into which the nanoparticle-containing solution would be injected was found in the vicinity of Jung-Wan of the mouse, a 31 gauge syringe-needle connected with micro-injector (KD Scientific, KDS310 NanoPump) and micro-manipulator was inserted into the subcutaneous tissue. It was preferable that the syringe needle had an angle of 10 to 20 degrees from the skin surface through which the nanoparticle-containing solution would be injected. Then, the nanoparticle-containing solution prepared in the Preparation Example 2 was injected in an amount of 0.2 ml by means of the syringe-needle and this process was performed under the stereoscopic microscope. It should be prevented that the syringe needle perforates through the muscular layer and the nanoparticle-containing solution flows into the abdominal cavity.

In order to check out whether nanoparticles arrived at internal organs, the skin of the abdominal side was incised with scissors and the linea alba was checked out and, then, from the xiphoid process to the pubic tubercle was incised along the linea alba by means of scissors. Attention should be paid so as not to bleed, and in case of bleeding, it could be prevented by means of a bleeding prevention forcep.

The mouse were moved to under the fluorescence microscope and the abdomen thereof was cut open and, then, flow of the nanoparticle-containing solution into the abdominal wall side surfaces of the organs including the liver, the stomach, the colitis and the small intestine was verified by such surfaces being observed. If the syringe needle perforated through the muscular layer and, thereby, the nanoparticle-containing solution was injected under the muscular layer to flow into the abdominal cavity, stain of the nanoparticle-containing solution on the surface of the organ could be observed. In this case, since the injection of the nanoparticle-containing solution was not properly performed, the experiment should be repeated.

If the nanoparticle-containing solution was not observed on the abdominal wall side surfaces of the organs, the portion of the pancreas should be observed. After it was confirmed that the nanoparticle-containing solution gathered at the threadlike structures penetrating out through the surface of the pancreas and consisting of streak form of fat tissue in combination with blood vessels, the images were observed and photographed with the fluorescence microscope and the CCD camera at certain magnifications. The images wherein the threadlike structures having the nanoparticle-containing solution distributed therein penetrated back into the pancreas (FIG. 3) and into the side of the spleen (FIG. 4) were observed and photographed with the fluorescence microscope.

The nanoparticle-containing solution might appear at the interface tissue of the pancreas tail (FIG. 3, a thick arrow).

Although the examples of the present invention demonstrate the movement of solution (liquid agents) from Jung-Wan to the pancreas, the present invention is not restricted thereto and can be applied to methods of delivering solution from the different acupuncture points to the different internal organs. In this case, any liquid solution including any liquid material like medicine as well as the visualizing agents can be useful.

What is claimed is:

1. A method of visualizing arrival of liquid agents, comprising steps of: finding a point having the lowest electric resistance in a skin in the vicinity of Jung-Wan using an electro acupuncture point detector; injecting visualizing liquid material into the skin corresponding to the point having the lowest electric resistance using of an injecting instrument; and verifying the visualizing material reached at least one point of the pancreas and the threadlike structures on top of the surface of the pancreas.

2. The method of claim 1, further comprising a step of: after the step of verifying the visualizing liquid material, photographing tissue having the visualizing liquid material distributed therein using a microscope to acquire images thereof.

3. The method of claim 1, wherein the step of injecting the visualizing liquid material includes inserting a needle of the injecting instrument into the subcutaneous tissue under a stereoscopic microscope.

4. The method of claim 1, wherein the visualizing liquid material is one selected from of an alcian blue solution and a nanoparticle-containing solution labeled with fluorescent organic material.

5. The method of claim 4, wherein the alcian blue solution is prepared by dissolving an alcian blue powder into phosphate buffered saline, filtering the alcian blue solution through polystyrene filter, and keeping the filtered alcian blue solution in a cold state.

6. The method of claim 4, wherein the step of injecting the visualizing liquid material includes injecting the alcian blue solution in an amount of 0.1 μl/min for 2 to 3 hours using the injecting instrument.

7. The method of claim 4, wherein the step of injecting the visualizing liquid material includes injecting the nanoparticle-containing solution labeled with fluorescent organic material in an amount of 0.2 ml using of the injecting instrument.

8. The method of claim 2, wherein the microscope is one selected from stereoscopic microscope and a fluorescence microscope.

* * * * *